United States Patent [19]

Lapidus et al.

[11] 4,209,441

[45] Jun. 24, 1980

[54] ANTI-GASTRIC SECRETION POLYPEPTIDE

[75] Inventors: Milton Lapidus, Rosemont; Victor M. Garsky, Radnor, both of Pa.

[73] Assignee: American Home Products Corporation, New York, N.Y.

[21] Appl. No.: 25,504

[22] Filed: Mar. 30, 1979

[51] Int. Cl.$^2$ .................... C07C 103/52; H61K 37/00
[52] U.S. Cl. ............................. 260/112.5 S; 424/177
[58] Field of Search ................. 260/112.5 S; 424/177

[56] References Cited
PUBLICATIONS

J. Rivier, et al., Biochem. and Biophys. Res. Commun. 65, 1975, 746–750.

J. Rivier, et al., J. Med. Chemistry 1976 19, 1010–1013.

*Primary Examiner*—Delbert R. Phillips
*Attorney, Agent, or Firm*—George Tarnowski

[57] ABSTRACT

The polypeptide having the formula:

$$\begin{array}{c} \text{H—Ala—Gly—Cys—Lys—Asn—Phe—Phe—D—Trp—} \\ | \\ \text{S——————————S} \\ | \\ \text{Lys—Thr—Tyr—Thr—Ser—Cys—OH} \end{array}$$

which inhibits gastric secretion without suppressing secretion of insulin and glucagon.

1 Claim, No Drawings

ANTI-GASTRIC SECRETION POLYPEPTIDE

BACKGROUND OF THE INVENTION

It is known that crude hypothalmic preparations will inhibit the secretion of the growth hormone, somatotropin. The somatotropin-release-inhibiting factor (SRIF) responsible for this activity was isolated and its structure elucidated by Brazeau et al., Science, 179, 77 (1973) as:

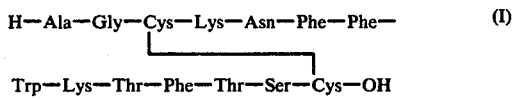

This tetradecapeptide is commonly referred to as somatostatin.

Somatostatin has also been found to inhibit the thyrotropin releasing hormone-induced release of thyrotropin in vivo in humans (Siler et al., J. Clin. Endocrinol. Metab., 38, 742, 1974), as well as inhibiting insulin (Mortimer et al., Lancet, 1, 697, 1974; Yen et al., New England J. Med., 290, 935, 1974); glucagon (Ginch et al., New England J. Med., 291, 544, 1974; Mortimer et al., ibid.) and gastrin (Bloom et al. Lancet, 2, 1106, 1974) secretion in vivo in humans. A direct somatostatin effect in the pancreatic cells or stomach has been confirmed under in vitro conditions for insulin (Mortimer et al., ibid), glucagon (Gerich et al., Endocrinology, 96, 749, 1975; Johnson et al., Endocrinology, 96, 370, 1975) and gastrin (Hayes et al., Endocrinology, 96, 1374, 1975).

In U.S. Pat. No. 4,061,626, somatostatin, D-Lys$^4$-SRIF and D-Ala$^2$, D-Lys$^4$-SRIF are disclosed as gastric acid secretion inhibitors, as well as inhibitors of growth hormone, glucagon and insulin secretion. U.S. Pat. No. 4,062,816 discloses the activity of D-Ala$^5$-SRIF as an inhibitor of gastric acid secretion as well as an inhibitor of growth hormone secretion. Lippmann et al., Pharmac. Res. Comm., 8, 445 (1976) discloses gastric acid secretion inhibition by somatostatin and several analogs.

The present invention relates to a novel synthetic polypeptide which does not suppress insulin or glucagon, but selectively suppresses gastric secretion, and which may be characterized as an analog of somatostatin.

DETAILED DESCRIPTION OF THE INVENTION

The invention comprises a polypeptide having the formula:

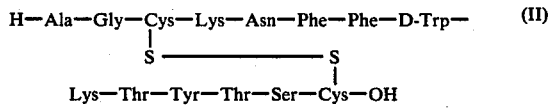

and pharmaceutically acceptable salts thereof.

Non-toxic, pharmaceutically acceptable salts of the reduced linear and cyclic polypeptides are produced by methods known to the art from such organic and inorganic acids are hydrochloric, hydrobromic, sulfuric, phosphoric, polyphosphoric, maleic, acetic, citric, benzoic, succinic, malonic, ascorbic. Acetic acid salts are most commonly employed and to that extent are preferred.

All optically active amino acid residues in the polypeptide of Formula II, and of those described herein, are in the natural or L-configuration, unless otherwise noted.

The compound of Formula II functions as an antisecretory agent to reduce (1) total gastric volume, (2) hydrogen ion secretion, or (3) hydrogen ion concentration. The reduction in any one of these parameters aids in attenuating the general debilitating influence of a peptic ulcer. The use of compounds exhibiting antisecretory activity in the curative and/or prophylactic treatment of peptic ulcer disease is an established, beneficial procedure.

The polypeptide of this invention is produced by the well known solid phase method as described by Stewart et al., Solid Phase Peptide Synthesis, Freeman and Co., San Francisco, 1969. As applied to the compound of this invention, α-amino and sulfhydryl protected cysteine is attached to a chloromethylated polystyrene resin followed by removal of the α-amino protecting group with trifluoroacetic acid in methylene chloride, trifluoroacetic acid alone or hydrogen chloride in dioxane. The deprotection is conducted at a temperature between about 0° C. and room temperature. Other standard cleaving reagents and conditions for removal or specific α-amino protecting groups may be used as described in Schroder E. Lubke, "The Peptides", 1, 72–75 (Academic Press, 1965). After removal of the α-amino protecting group the subsequent protected amino acids are coupled individually to the resin supported sequence, seriatim. Alternatively, small peptide fragments may be prepared by the solution method and introduced into the solid phase reactor in the desired order. Each protected amino acid or amino acid sequence is introduced into the solid phase reactor in about a four fold excess. The coupling is carried out in dimethylformamide, methylene chloride, or a mixture of the two solvents. The success of each coupling reaction at each stage of the synthesis is determind by the ninhydrin reaction as described by E. Kaiser et al., Analyt. Biochem., 34, 595 (1970). Where incomplete coupling has occurred, the reaction is repeated before the α-amino protecting group is removed for introduction of the next amino acid or amino acid sequence. The preferred coupling reagents are N-hydroxybenzotriazole and diisopropylcarbodiimide.

After the desired amino acid sequence has been synthesized, the polypeptide is removed from the resin support by treatment with, for example, hydrogen fluoride and anisole to obtain the fully deprotected linear polypeptide. The cyclic disulfide may be produced by air oxidation, or for example, by oxidation with $K_3Fe(CN)_6$.

Non-toxic acid addition salts of the linear and cyclic polypeptides are produced by methods well known in the art from hydrochloric, hydrobromic, sulfuric, phosporic, polyphosphoric, maleic, acetic, citric, benzoic, succinic, malonic, or ascorbic acid and the like.

The protecting groups employed throughout the solid phase synthesis are well known to the art. In selecting a particular side chain protecting group to be used in the synthesis of the peptides of this invention, the following rules should be followed: (a) the side chain protecting group must be stable to the reagent and under the reaction conditions selected for removing the α-amino protecting group at each step of the synthesis, (b) the protecting group must retain its protecting properties (i.e. not be split off under coupling conditions), and (c) the side chain protecting group must be removable upon the completion of the synthesis containing the desired amino acid sequence under reaction conditions that will not alter the peptide chain.

The α-amino protecting groups employed with each amino acid introduced in sequence of the ultimate polypeptide are of the (1) acyl type protecting groups illustrated by the following: formyl, trifluoroacetyl, phthalyl, p-toluenesulfonyl (tosyl), nitrophenylsulfenyl, etc.; (2) aromatic urethane type protecting groups illustrated by benzyloxycarbonyl and substituted benzyloxycarbonyl such as p-chlorobenzyloxycarbonyl, p-nitrobenzyloxycarbonyl; (3) aliphatic urethane protecting groups illustrated by tert-butyloxycarbonyl, diisopropylmethoxycarbonyl, isopropyloxycarbonyl, allyloxycarbonyl, 2,2,2-trichloroethoxycarbonyl, amyloxycarbonyl; (4) cycloalkyl urethane type protecting groups illustrated by cyclopentyloxycarbonyl, adamantyloxycarbonyl, cyclohexyloxycarbonyl; (5) thiourethane type protecting groups such as phenylthiocarbonyl; (6) alkyl type protecting groups as illustrated by triphenylmethyl (trityl); (7) trialkylsilane groups such as trimethylsilane. The preferred α-amino protecting group is tert-butyloxycarbonyl.

Protection for the side chain amino group of lysine may be by tosyl, t-amyloxycarbonyl, t-butyloxycarbonyl, diisopropyloxycarbonyl, benzyloxycarbonyl, halobenzyloxycarbonyl, nitrobenzyloxycarbonyl, and the like, the 2-chlorobenzyloxycarbonyl group being preferred.

Protection for the hydroxyl group of threonine and serine may be with the acetyl, benzoyl, tert-butyl, benzyl. The benzyl group is preferred for this purpose.

The protecting group for the sulfhydryl group of the cysteinyl amino acid residue is a group selected from the class consisting of benzyl; substituted benzyl wherein the substituent is at least one of methyl, methoxy, nitro, or halo (e.g. 3,4-dimethylbenzyl, p-methoxybenzyl, p-chlorobenzyl, p-nitrobenzyl, etc.); trityl, benzyloxycarbonyl, benzhydryl, p-methoxybenzyloxycarbonyl, benzylthiomethyl, ethylcarbamoyl, thioethyl, tetrahydropyranyl, acetamidomethyl, benzoyl, s-sulfonic salt, etc.; the p-methoxybenzyl group being preferred.

The polypeptide of this invention was tested and found active parenterally (s.c.) in the following scientifically recognized, standard test for anti-secretory activity;

Male Charles River rats of Sprague-Dawley strain and 190 to 240 gm. body weight are food deprived for 24 hr. with water ad libitum until the test. Groups of ten rats each are assigned to either control or drug treatment. Pyloric ligation was performed under ether anesthesia through a midline laparotomy, and either control vehicle (0.25 methylcellulose) or drug in control vehicle was administered intraduodenally. The rats are sacrificed by $CO_2$ asphyxiation four hours after pyloric ligation. The stomachs are removed and the gastric contents emptied into graduated centrifuge tubes. The gastric samples are centrifuged for 20 min. and those obviously contaminated by food, blood or feces are discarded. The volume of gastric fluid is recorded and the acid concentration of 1.0 ml. sample aliquots is measured by electrometric titration to pH 7.0 with 0.1 N NaOH. The calculated product of gastric volume (ml/4 hr.) and acid concentration (mEq/L) estimates the total acid output (TAO, mEq/4 hr.) over the four-hour test period. An analysis of variance is performed on these data to determine statistically significant ($p < 0.05$) deviation between control versus drug-treated groups.

Thus, the anti-secretory agent of this invention is of use in treating peptic ulcer disease by administering it, parenterally to a mammal in need thereof in an amount sufficient to alleviate the debilitating effects of said disease. The polypeptide may be administered neat or as a composition. Suitable liquid compositions include sterile solutions for parenteral administration. The polypeptide may be employed alone as the sole basis for treatment or it may be advantageously employed in conjunction with a treatment regimen utilizing a conventional antacid such as calcium carbonate, magnesium carbonate, bismuth carbonate, aluminum or magnesium hydrated oxides, magensium glycinate, magnesium trisilicate, calcium trisilicate, or sodium bicarbonate to maintain gastric acidity from about a pH of 3 to 5 or higher. Likewise, the anti-secretory agent of this invention may be used in conjunction with known anticholinergic agents or known $H_2$-receptor blocking agents.

The pharmaceutical compositions containing the anti-secretory agent of this invention are formulated conventionally with a sterile liquid carrier. Unit dosage forms containing from about 1 to 50 milligrams of polypeptide are especially suitable.

As with any gastric ulcer disease treatment, the dosage and treatment regimen employing an anti-secretory agent is entirely subjective and must be regulated by the physician to the individual patients need subject to such variables as age, severity of the condition, mode of administration, companion medication, response to the treatment, etc. Therefore, the dose of polypeptide to be employed in any given case must be determined by the attending physician.

Although the compound of this invention is an analogue of somatostatin, it demonstrates no meaningful reduction in insulin or glucagon when tested in vivo by standard methods. Hence, it affords effective means for combatting peptic ulcer disease where no concomitant reduction in secretion insulin and glucagon is desired.

An index of drug gastric antisecretory activity is reported at the end of the example illustrating its production. The results, expressed as percentage inhibition, show the reduction of acid secretion in drug-treated compared to control groups, based upon i.d. administration of 2 mg/kg and 0.5 mg/kg of the tested compound. In addition, the effect of the polypeptide in the control of insulin and glucagon secretion is reported at a dose of 750 micrograms per kilogram. Somatostatin effectively inhibit secretion of insulin and glucagon in that test procedure at about 10 micrograms per kilogram.

The following Examples illustrate the preparative techniques applicable in the production of the compounds of the invention.

EXAMPLE 1 t-Butyloxycarbonyl-S-p-Methoxybenzyl-L-cysteine Resin Ester

In a 2.1 round bottom reaction vessel is mixed a solution of t-butyloxycarbonyl-S-p-methoxybenzyl-L-cysteine (34.1 g., 0.1 mole) in 500 ml. of purified dimethyl sulfoxide, a solution of potassium tertiary butoxide (10 g., 0.09 mole) in 200 ml. of purified dimethyl sulfoxide, and chloromethylated polystyrene resin (Bio Rad S-X1 polystyrene beads, 200–400 mesh)(50 g., 37.5 meq.). The volume is adjusted to 1 l. with dimethyl sulfoxide and the mixture is stirred and maintained at 80° for 1½ hours. After cooling to 50° the t-butyloxycarbonyl-S-p-methoxybenzyl-L-cysteine polystyrene resin ester is collected in a sintered glass funnel and is washed with 200 ml. of the following solvents: ethanol three times, methanol three times, methylene chloride three times, methanol twice and methylene chloride three times. Residual solvents are removed by drying the product in a vacuum oven at room temperature. Product yield is 61 g.

EXAMPLE 2 t-Butyloxycarbonyl-O-benzyl-L-threonyl-O-benzyl-L-seryl-S-p-methoxybenzyl-L-cysteine resin ester To a 200 ml. reaction vessel are added 24.6 g. of the t-butyloxycarbonyl-S-p-methoxybenzyl-L-cysteine resin ester of Example 1. The resin is then treated in the following manner to deprotect the amino group:

(a) wash with methylene chloride (three times);
(b) 5 minute prewash with 38% trifluoroacetic acid/-methylene chloride (v/v) containing 0.5% dithioerythritol.
(c) 25 minute treatment with the solution of step (b) above;
(d) wash with methylene chloride (three times);
(e) wash with dimethylformamide (three times);
(f) 1 minute treatment with 15% triethylamine in dimethylformamide;
(g) 10 minute treatment with the solution of step (f) above;
(h) wash with dimethylformamide (three times); and
(i) wash with methylene chloride (three times).

A contact time of 2 minutes stirring is allowed for each wash (a-i) unless noted. The amino acid resin is subjected to ninhydrin color test following the procedure of E. Kaiser et al., Analytical Biochemistry, 34, 595, (1970) and is found to be positive. This is a positive test for deprotection.

(j) The resin is next gently stirred with t-butyloxycarbonyl-O-benzyl-L-serine (8.856 g., 30 meq.) in 150 ml. of 1:1 dimethylformamide methylene chloride and N-N'-diisopropyl carbodiimide, (33 mmoles, 1 mmole/ml. methylene chloride) overnight. The resin is then washed in the following sequence:
(k) dimethylformamide (three times);
(l) methanol (three times); and
(m) methylene chloride (three times).

A negative ninhydrin color test on approximately 50 mg. of resin following the procedure of E. Kaiser indicates the reaction is complete and that t-butyloxycarbonyl-L-seryl-S-p-methoxybenzyl-L-cysteine resin ester is the intermediate prepared.

Removal of the t-butyloxycarbonyl-α-amino protecting group is carried out as described in steps (a) through (i) above. t-Butyloxycarbonyl-O-benzyl-L-threonine is added next as in step (j). Following the reaction, steps (k) through (m) are completed and the title resin product is dried in a vacuum oven at room temperature to yield 26.8 g. of product with 0.19 mmoles of amino acid residues per gram of resin.

A full cycle for the addition of an amino acid to the growing chain is steps (a) through (m).

EXAMPLE 3 t-Butyloxycarbonyl-L-alanylglycyl-S-p-methoxybenzyl-L-cysteinyl-ε-chlorobenzyloxycarbonyl-L-lysyl-L-asparaginyl-L-phenylalanyl-L-phenylalanyl-D-trypotpyl-ε-chlorobenzyloxycarbonyl-L-lysyl-O-benzyl-L-threonly-O-benzyl-L-tyrosyl-O-benzyl-L-threonyl-O-benzyl-L-seryl-p-methoxybenzyl-L-cysteine resin ester To a 200 ml. reaction vessel is added 6.7 g. of the t-butyloxycarbonyl-O-benzyl-L-threonyl-O-benzyl-L-seryl-S-p-methoxybenzyl-L-cysteine resin ester of Example 2. A full cycle of steps (a) through (m) is used to introduce a new amino acid to the growing chain as explained in Example 2. The amino acid residues are introduced consecutively in the positions described below as follows (t-Boc means t-butyloxycarbonyl, Bzl means O-benzyl, and Z means benzyloxycarbonyl):

```
                    Bzl(OME)  Z(Cl)
                       |        |
t-Boc—Ala—Gly—Cys—Lys—Asn—Phe—Phe—D-Trp—
       14   13   12   11   10    9    8    7
   ┌────────────────────────────────────────┘
   │    6    5    4
   └—Lys—Thr—Tyr—Thr—Ser—Cys—O resin ester
        |    |    |    |    |    |
      (Cl)Z  Bzl  Bzl  Bzl  Bzl  Bzl(OMe)
```

4. t-Boc-(O-benzyl)-L-Tyrosine (2.228 g., 6 mmoles)
5. t-Boc-(O-benzyl)-L-threonine (1.855 g., 6 mmoles)
6. t-Boc-(ε-chloro-benzyloxycarbonyl)-L-lysine (2.487 g., 6 mmoles)
7. t-Boc-D-tryptophan (1.824 g., 6 mmoles)
8. t-Boc-L-phenylalanine (1.592 g., 6 mmoles)
9. t-Boc-L-phenylalanine (1.592 g., 6 mmoles)
10. t-Boc-L-asparagine (2.320 g., 10 mmoles)
11. t-Boc-(ε-chlorobenzyloxycarbonyl)-L lysine (4.140 g., 10 mmoles)
12. t-Boc- (S-p-methoxybenzyl)-L-cysteine (3.410 g., 10 mmoles)
13. t-Boc-glycine (1.750 g., 10 mmoles)
14. t-Boc-L-alanine (1.892 g., 10 mmoles)

Each t-Boc-amino acid is coupled with a 1.1 equivalent of N-N'-diisopropylcarbodiimide in 150 ml. of 1:1 dimethylformamide methylene chloride overnight. Following each complete coupling (step j) the resin is washed (steps k-m). Removal of the t-Boc group is described in steps (a) - (i). After the final washing the resin is dried in vacuo at room temperature to yield 10.2 g.

EXAMPLE 4

L-Alanylglycyl-L-cysteinyl-L-lysyl-L-asparaginyl-L-phenylalanyl-L-phenylalanyl-D-tryptophyl-L-lysyl-L-threonyl-L-tyrosyl-L-threonyl-L-seryl-L-cysteine cyclic (3–14)-disulfide, triacetate-salt 10.2 g. of the title compound in Example 3 is treated in vacuo with anhydrous liquid hydrogen fluoride (100 ml.) and anisole (10ml.) at 0° for 1 hour. The hydrogen fluoride and anisole are removed under reduced pressure and the residue is dissolved in 100 ml. of 2 N acetic acid and collected under nitrogen into 4.1 of deaerated water. The solution is adjusted to pH 6.9 with dilute ammonium hydroxide and let stand in the cold room for a week. The solution is lyophilized and yields 3.1 g. of powder.

EXAMPLE 5

Purification and characterization of L-alanylglycyl-L-cysteinyl-L-lysyl-L-asparaginyl-L-phenylalanyl-L-phenylalanyl-D-tryptophyl-L-lysyl-L-threonyl-L-tyrosyl-L-threonyl-L-seryl-L-cysteine cyclic (3–14)-disulfide, triacetate-salt The crude nitroprusside-negative product of Example 4 is purified as follows: 3.1 g. of the compound of Example 4 is dissolved in 100 ml. of 50% acetic acid and applied to a column 2.5×200 cm. of Sephadex G 25 in 50% acetic acid. The column effuent is monitored automatically by means of a recorder and flow cell (254Mμ) while 4.5 ml. fractions are collected. Tubes 150–180 are collected and lyophilized to yield 570 mg. of product.

The product is further purified by partion chromatography. 570 mg. of product is dissolved in upper phase of n-butanol-water-acetic acid (4:5:1) and applied to a column of Sephadex G 25 SF (2.5×100 cm.)-upper phase. The column effuent collected in 2.5 ml. fractions is monitored as above. Fractions 135–170 are collected, solvent removed, and pure product lyophilized to yield 58 mg. The material is shown to be homogeneous by thin chromatograph system, Silica Gel-G developed with n-butanolethyl acetate-acetic acid-water (1:1:1:1). Thin layer chromatograms are visualized with chlorine peptide spray.

Amino acid analysis gives: Asp 1.01, Thr 1.88, Ser 0.79, gly 1.00, Ala 1.00, Cys 1.85, Tyr 0.90, Phe 1.97, Lys 1.93, Trp 0.36.

Percentage Inhibition: 2mg/kg - 68%, 0.5 mg/kg - 38% (of Total Acid Output)

Suppression of Glucagon and Insulin

Albino male rats are administered Nembutol intraperitoneally at a dose of 50 mg/kg. Fifteen minutes later a subcutaneous injection of the test compound or physiological saline is administered. Ten minutes later 0.5 ml. of arginine (300 mg/ml, pH 7.2) is injected into the heart. Five minutes after receipt of the arginine the rats are decapitated and blood is collected into Trasylol-EDTA. An appropriate aliquot is assayed for insulin and glucagon. The results of the assay are as follows:

| Compound | Dose (μg/kg) | Insulin (μU/ml) | Glucagon (pg/ml) |
|---|---|---|---|
| Control | — | 283 ± 28 | 55 ± 5 |
| Polypeptide of Invention | 750 | 238 ± 42 | 35 ± 9 |

Thus, the polypeptide of the invention is an effective agent for selectively reducing gastric secretion without materially affecting insulin and glucagon levels.

What is claimed is:

1. A polypeptide of the formula:

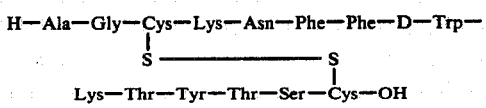

and pharmaceutically acceptable salts thereof.